United States Patent [19]

Maienfisch et al.

[11] Patent Number: 4,946,854
[45] Date of Patent: Aug. 7, 1990

[54] 3-AMINOBENZOYLPHENYLUREAS USEFUL FOR CONTROLLING PARASITES AND INSECTS THAT ATTACK DOMESTIC ANIMALS AND LIVESTOCK

[75] Inventors: Peter Maienfisch; Jean-Claude Gehret, both of Aesch; Bruno Frei, Lausen, all of Switzerland

[73] Assignee: Ciba-Geigy Corporation, Ardsley, N.Y.

[21] Appl. No.: 280,061

[22] Filed: Dec. 5, 1988

[30] Foreign Application Priority Data

Dec. 7, 1987 [CH] Switzerland .......................... 4756/87

[51] Int. Cl.$^5$ ..................... C07D 213/64; A01N 43/40
[52] U.S. Cl. ..................................... 514/346; 546/291; 546/300; 546/306; 546/294; 560/355; 564/166
[58] Field of Search .......................... 546/291; 514/346

[56]  References Cited
FOREIGN PATENT DOCUMENTS 230400  1/1987  European Pat. Off. ............ 546/291
3240975  5/1983  Fed. Rep. of Germany ...... 546/291

Primary Examiner—Alan L. Rotman
Attorney, Agent, or Firm—Kevin T. Mansfield; Edward M. Roberts

[57] ABSTRACT

Novel compounds of formula I

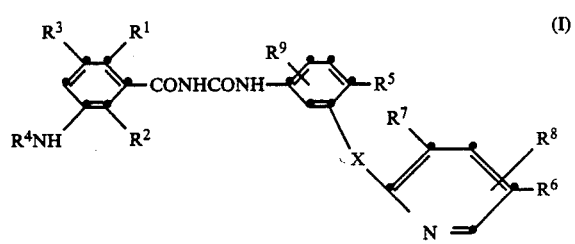

wherein
each of $R^1$, $R^2$, $R^3$, $R^7$, $R^8$ and $R^9$, independently of the others, is H or halogen,
$R^4$ is H, $R^{10}$CO— or $R^{11}$NHCO— wherein $R^{10}$ is a $C_1$–$C_4$alkyl group which is unsubstituted or substituted by one to three identical or different substituents selected from the group consisting of halogen, $C_1$–$C_4$alkoxy, $C_1$–$C_4$- acyloxy and —COOG, wherein G is H, an alkali metal cation or an alkaline earth metal cation, and $R^{11}$ is an unsubstituted or halo-substituted $C_1$–$C_4$alkyl or phenyl group,
each of $R^5$ and $R^6$, independently of the other, is H, halogen, alkyl or haloalkyl and
X is O, S(O)n or NH wherein n is 0, 1 or 2, the preparation of the novel compounds and their use against parasites in and on productive livestock and against insect pests, and novel starting materials and their preparation.

22 Claims, No Drawings

3-AMINOBENZOYLPHENYLUREAS USEFUL FOR CONTROLLING PARASITES AND INSECTS THAT ATTACK DOMESTIC ANIMALS AND LIVESTOCK

The present invention relates to novel benzoylphenylureas that have a substituted or unsubstituted amino group in the 3-position of the benzoyl moiety, to processes for their preparation and to their use in pest control. The invention relates also to novel starting materials and their preparation.

The substituted 3-aminobenzoylphenylureas according to the invention have the formula I

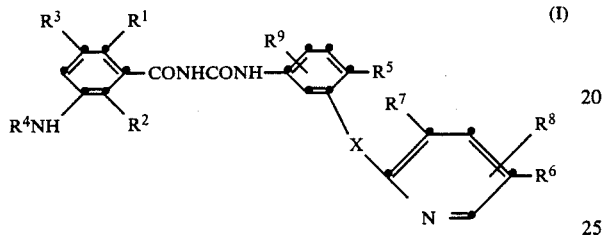

wherein
each of $R^1$, $R^2$, $R^3$, $R^7$, $R^8$ and $R^9$, independently of the others, is H or halogen,
$R^4$ is H, $R^{10}CO—$ or $R^{11}NHCO—$ wherein $R^{10}$ is a $C_1$–$C_4$alkyl group which is unsubstituted or substituted by one to three identical or different substituents selected from the group consisting of halogen, $C_1$–$C_4$alkoxy, $C_1$–$C_4$acyloxy and —COOG, wherein G is H, an alkali metal cation or an alkaline earth metal cation, and $R^{11}$ is an unsubstituted or halo-substituted $C_1$–$C_4$alkyl or phenyl group,
each of $R^5$ and $R^6$, independently of the other, is H, halogen, alkyl or haloalkyl and
X is O, S(O)n or NH wherein n is 0, 1 or 2.

Within the scope of the present invention, halogen as an independent substituent or as part of a substituent shall be understood as being fluorine, chlorine, bromine or iodine, preferably fluorine, chlorine or bromine, and especially fluorine or chlorine.

Alkyl groups as independent substituents or as part of a substituent may be straight-chained or branched. Unless otherwise defined, alkyl is preferably $C_1$–$C_6$alkyl, for example methyl, ethyl, propyl, isopropyl, butyl, isobutyl, sec.-butyl, tert.-butyl, n-pentyl and n-hexyl. Preferred are alkyl groups having 1 to 4 carbon atoms, especially methyl and ethyl.

Suitable haloalkyl groups are halogenated alkyl radicals wherein the alkyl radical corresponds to the definitions given above and is partially or completely halogenated. Examples of such groups are $CF_3$, $CCl_3$, $C_2H_4F$, $CF_2CCl_2F$, preferably $CF_3$ and $CF_2CCl_2F$, especially $CF_3$. $C_1$–$C_4$acyloxy shall be understood as being a radical selected from the group consisting of $C_1$–$C_3$alkyl—COO—, $C_1$–$C_3$alkenyl—COO—, $C_1$–$C_3$alkynyl—COO— and cyclopropyl—COO—. Alkyl may be methyl, ethyl or propyl, alkenyl may be, for example, vinyl or methylvinyl and alkynyl may be, for example, ethynyl or propynyl.

Suitable alkali metal cations G are, for example, sodium, potassium and lithium cations and suitable alkaline earth metal cations G are, for example, magnesium, calcium and barium cations. Calcium and, especially, sodium cations are preferred.

Especially interesting are compounds of formula I wherein
(a) $R^1$ is halogen, preferably fluorine or chlorine, especially fluorine;
(b) $R^2$ is halogen, preferably fluorine or chlorine, especially fluorine;
(c) $R^3$ is hydrogen, fluorine or chlorine, preferably hydrogen;
(d) $R^4$ is hydrogen, $R^{10}CO—$ or $R^{11}NHCO—$ wherein $R^{10}$ is $C_1$–$C_4$alkyl that is unsubstituted or substituted by —COOG, wherein G is hydrogen, an alkali metal cation or an alkaline earth metal cation, and $R^{11}$ is an unsubstituted or halo-substituted $C_1$–$C_4$alkyl or phenyl group, the preferred meaning of $R^4$ being hydrogen.
(e) $R^5$ is hydrogen, halogen, $C_1$–$C_4$haloalkyl, preferably hydrogen, methyl, $CF_3$, fluorine, chlorine or bromine, especially fluorine or chlorine;
(f) $R^6$ is hydrogen, halogen, $C_1$–$C_4$alkyl or $C_1$–$C_4$haloalkyl, preferably hydrogen or $C_1$–$C_2$haloalkyl, especially $CF_3$;
(g) $R^7$ is hydrogen, fluorine, bromine or chlorine, preferably hydrogen, fluorine or chlorine, especially chlorine;
(h) $R^8$ is hydrogen, fluorine, bromine or chlorine, preferably hydrogen, fluorine or chlorine, especially hydrogen;
(i) $R^9$ is hydrogen, fluorine, bromine or chlorine, preferably hydrogen, fluorine or chlorine, especially hydrogen; or
(j) X is sulfur, NH or oxygen, preferably oxygen.

Compounds of formula I that are of interest owing to their pesticidal activity are those belonging to one of the following groups wherein (a) $R^1$ and $R^2$ are halogen, $R^4$ is hydrogen, $R^{10}CO—$ or $R^{11}NHCO—$ wherein $R^{10}$ is $C_1$–$C_4$alkyl that is unsubstituted or substituted by —COOG, each of $R^5$ and $R^6$, independently of the other, is hydrogen, halogen, $C_1$–$C_4$alkyl or $C_1$–$C_4$haloalkyl and each of $R^7$, $R^8$ and $R^9$, independently of the others, is hydrogen, fluorine, bromine or chlorine, and $R^3$, $R^{11}$, G and X are as defined in formula I; (b) each of $R^1$ and $R^2$, independently of the other, is fluorine or chlorine, $R^3$ is hydrogen, fluorine or chlorine, $R^4$ is hydrogen, $R^5$ is hydrogen, methyl, $CF_3$, fluorine, chlorine or bromine, $R^6$ is hydrogen or $C_1$–$C_2$haloalkyl, each of $R^7$, $R^8$ and $R^9$, independently of the others, is hydrogen, fluorine or chlorine and X is sulfur or oxygen; (c) each of $R^1$ and $R^2$, independently of the other, is fluorine or chlorine, $R^3$ is hydrogen, $R^4$ is hydrogen, —COCH$_3$, —COCH$_2$CH$_2$COOH or —CONHCH$_3$, $R^5$ is hydrogen, fluorine, chlorine or methyl, $R^6$ is $CF_3$ or $CF_2CCl_2F$, each of $R^7$ and $R^8$, independently of the other, is hydrogen or chlorine, $R^9$ is hydrogen or fluorine and X is oxygen, sulfur or NH; (d) $R^5$ is fluorine or chlorine, $R^6$ is $CF_3$, $R^7$ is chlorine, $R^8$ and $R^9$ are hydrogen and X is oxygen and $R^1$ to $R^4$ are as defined in group (c); or (e) $R^1$ and $R^2$ are fluorine, $R^3$ and $R^4$ are hydrogen, $R^5$ is fluorine or chlorine, $R^6$ is $CF_3$, $R^7$ is chlorine, $R^8$ and $R^9$ are hydrogen and X is oxygen.

Special mention should be made of the compounds N-[3-(3-chloro-5-trifluoromethylpyridyl-2-oxy)-4-chlorophenyl]-N'-[2,6-difluoro-3-aminobenzoyl]-urea and N-[3-(3-chloro-5-trifluoromethylpyridyl-2-oxy)-4-fluorophenyl]-N'-[2,6-difluoro-3-aminobenzoyl]-urea.

Benzoylureas are known per se as active ingredients in pesticidal compositions; for example, N-[3-(pyridyl-2-oxy)-phenyl]-N'-benzoylureas are disclosed in EP 0,079,311 (=U.S. Pat. No. 4,677,127) as insecticides and acaricides. Surprisingly, it has now been found that the introduction of a 3-amino group into the benzoyl moiety results in distinctly more favourable physico-chemical properties (for example increased solubility in protic solvents) and, in particular, distinctly improved bioavailability after systemic administration to warm-blooded animals. With the compounds according to the invention, on the one hand high blood plasma values are achieved immediately after administration and, on the other hand, a very much faster degradation or a rapid excretion of the active ingredient is achieved. The compounds according to the invention are considerably better suited to achieving an immediate effect with a full degree of efficacy than the mentioned compounds of the prior art.

The compounds of formula I can be prepared as follows:
  (a) compounds of formula I wherein $R^4$ is H can be obtained by
    (i) hydrogenating a compound of formula II

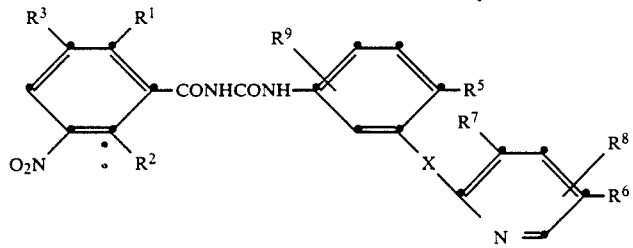

(II)

wherein $R^1$ to $R^9$ and X are as defined above, in the presence of a suitable catalyst and at normal pressure of $H_2$ or
    (ii) chemical reduction of a compound of formula II;
  (b) compounds of formula I wherein $R^4$ is $R^{10}CO-$ or $R^{11}NHCO-$ can be prepared by reacting compounds of formula I wherein $R^4$ is H with an acid, an acid halide, an acid anhydride or with an isocyanate.

The said processes (ai), (aii) and (b) are preferably carried out in the presence of an organic solvent or diluent. Suitable solvents and diluents are, for example, ethers (including tetrahydrofuran), esters and alcohols, in the case of processes (ai) and (aii), and ethers, or aliphatic or aromatic hydrocarbons that are unsubstituted or substituted by substituents selected from the group consisting of halogen and $C_1$–$C_4$alkyl, preferably methyl, especially benzene, toluene, xylene, chloroform, methylene chloride, carbon tetrachloride and chlorobenzene, in the case of process (b). The processes are generally carried out at a temperature of 0° to 80° C. In the case of processes (ai) and (aii), a temperature of 10° to 50° C. is preferred, and in the case of process (b) 20° to 50° C. Process (b) is generally carried out in the presence of an organic base, for example pyridine. A suitable catalyst for process (ai) is, for example, 5% Rh/C or Raney nickel. The chemical reduction according to process (aii) can be carried out, for example, by treating a compound of formula II with Sn(II) chloride/HCl. In process (b), an acid, an acid halide or an acid anhydride shall be understood as being $R^{10}COOH$, the corresponding acid halide or anhydride and an isocyanate shall be understood as being $R^{11}NCO$.

The starting materials of formula II are novel and the present invention relates also to these. Especially interesting are compounds of formula II wherein
  (a) $R^1$ is halogen, preferably fluorine or chlorine, especially fluorine;
  (b) $R^2$ is halogen, preferably fluorine or chlorine, especially fluorine;
  (c) $R^3$ is hydrogen, fluorine or chlorine, preferably hydrogen;
  (d) $R^5$ is hydrogen, halogen, $C_1$–$C_4$alkyl or $C_1$–$C_4$haloalkyl, preferably hydrogen, methyl, $CF_3$, fluorine, chlorine or bromine, especially fluorine or chlorine;
  (e) $R^6$ is hydrogen, halogen, $C_1$–$C_4$alkyl or $C_1$–$C_4$haloalkyl, preferably hydrogen or $C_1$–$C_2$haloalkyl, especially $CF_3$;
  (f) $R^7$ is hydrogen, fluorine, bromine or chlorine, preferably hydrogen, fluorine or chlorine, especially chlorine;
  (g) $R^8$ is hydrogen, fluorine, bromine or chlorine, preferably hydrogen, fluorine or chlorine, especially hydrogen;
  (h) $R^9$ is hydrogen, fluorine, bromine or chlorine, preferably hydrogen, fluorine or chlorine, especially hydrogen; or
  (i) X is sulfur, NH or oxygen, preferably oxygen.

Of interest are those compounds of formula II which belong to one of the following groups wherein (a) $R^1$ and $R^2$ are halogen, each of $R^5$ and $R^6$, independently of the other, is hydrogen, halogen, $C_1$–$C_4$alkyl or $C_1$–$C_4$haloalkyl and each of $R^7$, $R^8$ and $R^9$, independently of the others, is hydrogen, fluorine, bromine or chlorine and $R^3$ and X are as defined in formula II; (b) each of $R^1$ and $R^2$, independently of the other, is fluorine or chlorine, $R^3$ is hydrogen, fluorine or chlorine, $R^5$ is hydrogen, methyl, $CF_3$, fluorine, chlorine or bromine, $R^6$ is hydrogen or $C_1$–$C_2$haloalkyl, each of $R^7$, $R^8$ and $R^9$, independently of the others, is hydrogen, fluorine or chlorine and X is sulfur, NH or oxygen; (c) each of $R^1$ and $R^2$, independently of the other, is fluorine or chlorine, $R^3$ is hydrogen, $R^5$ is hydrogen, fluorine, chlorine or methyl, $R^6$ is $CF_3$ or $CF_2CCl_2F$, each of $R^7$ and $R^8$, independently of the other, is hydrogen or chlorine, $R^9$ is hydrogen or fluorine and X is oxygen, sulfur or NH; (d) $R^5$ is fluorine or chlorine, $R^6$ is $CF_3$, $R^7$ is chlorine, $R^8$ and $R^9$ are hydrogen and X is oxygen and $R^1$, $R^2$ and $R^3$ are as defined in (c); or (e) $R^1$ and $R^2$ are fluorine, $R^3$ is hydrogen, $R^5$ is fluorine or chlorine, $R^6$ is $CF_3$, $R^7$ is chlorine, $R^8$ and $R^9$ are hydrogen and X is oxygen.

Especially worthy of mention are the compounds N-[3-(3-chloro-5-trifluoromethylpyridyl-2-oxy)-4-chlorophenyl]-N'-[2,6-difluoro-3-nitrobenzoyl]-urea and N-[3-(3-chloro-5-trifluoromethylpyridyl-2-oxy)-4-fluorophenyl]-N'-[2,6-difluoro-3-nitrobenzoyl]-urea.

The compounds of formula II can be prepared analogously to known processes. Such processes are described, inter alia, in DE-OS 2 123 236, 2 601 780 and 3 240 975.

For example, the compounds of formula II can be obtained by reacting (a) an aniline of formula III

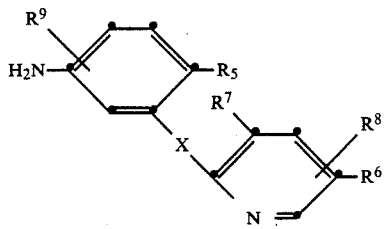

wherein $R^5$ to $R^9$ and X are as defined above, with a benzoyl isocyanate of formula IV

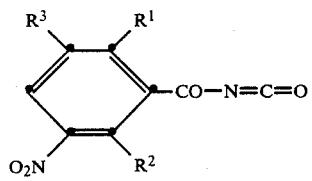

wherein $R^1$, $R^2$ and $R^3$ are as defined above, or (b) an isocyanate of formula V

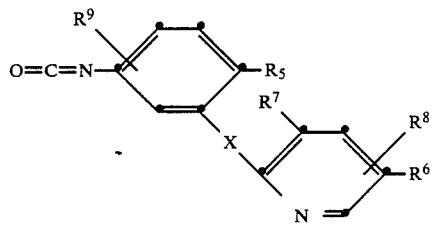

wherein $R^5$ to $R^9$ and X are as defined above, with a benzamide of formula VI

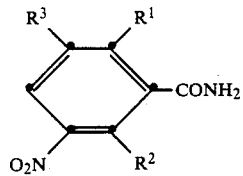

wherein $R^1$, $R^2$ and $R^3$ are as defined above, or (c) an aniline of formula III with a urethane of formula VII

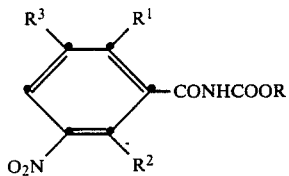

wherein $R^1$, $R^2$ and $R^3$ are as defined above and R is $C_1$-$C_5$alkyl or unsubstituted or nitro-substituted phenyl.

The said processes (a), (b) and (c) are preferably carried out under normal pressure and in the presence of an organic solvent or diluent. Suitable solvents and diluents are, for example, ethers and ethereal compounds, such as diethyl ether, dipropyl ether, dibutyl ether, dioxane, dimethoxyethane and tetrahydrofuran; N,N-dialkylated carboxylic acid amides; aliphatic or aromatic hydrocarbons that are unsubstituted or substituted by substituents selected from the group consisting of halogen and $C_1$-$C_4$alkyl, preferably methyl, especially benzene, toluene, xylene, chloroform, methylene chloride, carbon tetrachloride and chlorobenzene; nitriles, such as acetonitrile or propionitrile; dimethyl sulfoxide and ketones, such as acetone, methyl ethyl ketone, methyl isopropyl ketone and methyl isobutyl ketone. Process (a) is generally carried out at a temperature of $-10°$ to $+200°$ C., preferably $0°$ to $+100°$ C., for example at room temperature, optionally in the presence of an organic base, such as triethylamine. Process (b) is carried out at a temperature of $0°$ to $+150°$ C., preferably at the boiling point of the solvent used, and, optionally, in the presence of an organic base, such as pyridine. Temperatures of approximately $+60°$ up to the boiling point of the reaction mixture are preferred for process (c), that is to say, for the reaction of the urethane of formula VII with an aniline of formula III, there being used as solvent especially the above-mentioned unsubstituted or substituted aromatic hydrocarbons, such as toluene, xylenes or chlorobenzene.

The benzoyl isocyanates of formula IV can be prepared in accordance with generally customary processes from the benzamides of formula VI by reacting, for example, a compound of formula VI with oxalyl chloride in the presence of methylene chloride:

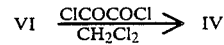

Urethanes of formula VII can be obtained analogously to known methods by reacting a benzoyl isocyanate of formula IV with a corresponding alcohol R-OH or by reacting a benzamide of formula VI in the presence of a basic compound with a corresponding ester of the chloroformic acid Cl—COOR wherein R is as defined above.

The substituted phenyl isocyanates of formula V can be prepared, for example, by treating the anilines of formula III with phosgene in accordance with generally customary processes.

The starting materials of formulae IV and VI are novel compounds to which the present invention also relates. Especially interesting are compounds of formulae IV and VI wherein (a) $R^1$ is halogen, preferably fluorine or chlorine, especially fluorine; or (b) $R^2$ is halogen, preferably fluorine or chlorine, especially fluorine.

Of interest are those compounds of formulae IV and VI wherein $R^1$ and $R^2$ are both halogen. Of particular interest are also those compounds of formulae IV and VI wherein each of $R^1$ and $R^2$, independently of the other, is fluorine or chlorine, especially those compounds of formulae IV and VI wherein $R^1$ and $R^2$ are fluorine, and $R^3$ is preferably hydrogen.

The compounds of formula VI can be prepared, for example, by nitrating compounds of formula VIII

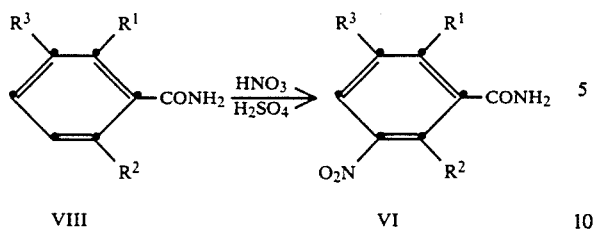

VIII → VI wherein $R^1$, $R^2$ and $R^3$ are as defined above.

The reaction is generally carried out at a temperature of −10° to +100° C., preferably 0° to 60° C.

The compounds of formula III with X=0 are known or can be prepared analogously to known processes, for example by reacting a corresponding 2-chloropyridinyl with a corresponding 3-hydroxyaniline analogously to the process described in DE-OS 3 240 975.

The starting materials of formula III with X=S(0)n or NH wherein n is 0, 1 or 2 are novel compounds to which the present invention also relates. Especially interesting among these compounds are those in which (a) $R^5$ is hydrogen, halogen, $C_1$-$C_4$alkyl or $C_1$-$C_4$-haloalkyl, preferably hydrogen, methyl, $CF_3$, fluorine, chlorine or bromine, especially fluorine or chlorine;

(b) $R^6$ is hydrogen, halogen, $C_1$-$C_4$alkyl or $C_1$-$C_4$-haloalkyl, preferably hydrogen or $C_1$-$C_2$haloalkyl, especially $CF_3$;

(c) $R^7$ is hydrogen, fluorine, bromine or chlorine, preferably hydrogen, fluorine or chlorine, especially chlorine;

(d) $R^8$ is hydrogen, fluorine, bromine or chlorine, preferably hydrogen, fluorine or chlorine, especially hydrogen; or (e) $R^9$ is hydrogen, fluorine, bromine or chlorine, preferably hydrogen, fluorine or chlorine, especially hydrogen, or which belong to one of the following groups wherein (a) each of $R^5$ and $R^6$, independently of the other, is hydrogen, halogen, $C_1$-$C_4$alkyl or $C_1$-$C_4$haloalkyl and each of $R^7$, $R^8$ and $R^9$, independently of the others, is hydrogen, fluorine, bromine or chlorine; (b) $R^5$ is hydrogen, methyl, $CF_3$, fluorine, chlorine or bromine, $R^6$ is hydrogen or $C_1$-$C_2$haloalkyl, and each of $R^7$, $R^8$ and $R^9$, independently of the others, is hydrogen, fluorine or chlorine; (c) $R^5$ is hydrogen, fluorine, chlorine or methyl, $R^6$ is $CF_3$, $R^7$ is hydrogen or chlorine, $R^8$ is hydrogen and X is sulfur or NH; or (d) $R^5$ is fluorine or chlorine, $R^6$ is $CF_3$, $R^7$ is chlorine, and $R^8$ and $R^9$ are hydrogen.

The compounds of formula III with X=S(0)n or NH can be prepared by reacting a compound of formula IX

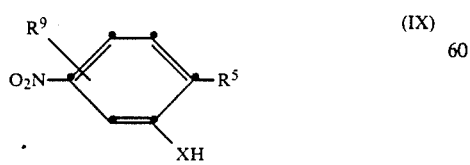

wherein $R^5$ and $R^9$ are as defined above and X is S(0)n or NH, wherein n is 0, with a compound of formula X

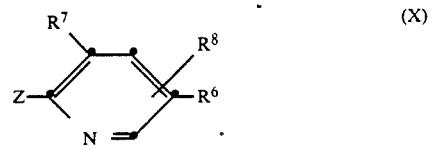

wherein $R^6$ to $R^8$ are as defined above and Z is halogen, and subsequently hydrogenating the resulting compound of formula XI

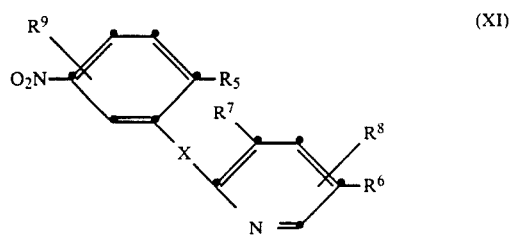

wherein $R^5$ to $R^9$ and X are as defined above.

The starting materials of formula XI are novel compounds to which the present invention also relates.

Especially interesting are compounds of formula XI wherein (a) $R^5$ is hydrogen, halogen, $C_1$-$C_4$alkyl or $C_1$-$C_4$-haloalkyl, preferably hydrogen, methyl, $CF_3$, fluorine, chlorine or bromine, especially fluorine or chlorine;

(b) $R^6$ is hydrogen, halogen, $C_1$-$C_4$alkyl or $C_1$-$C_4$-haloalkyl, preferably hydrogen or $C_1$-$C_2$haloalkyl, especially $CF_3$;

(c) $R^7$ is hydrogen, fluorine, bromine or chlorine, preferably hydrogen, fluorine or chlorine, especially chlorine;

(d) $R^8$ is hydrogen, fluorine, bromine or chlorine, preferably hydrogen, fluorine or chlorine, especially hydrogen;

(e) $R^9$ is hydrogen, fluorine, bromine or chlorine, preferably hydrogen, fluorine or chlorine, especially hydrogen; or (f) X is sulfur, NH or oxygen, preferably oxygen, or that belong to one of the following groups wherein (a) each of $R^5$ and $R^6$, independently of the other, is hydrogen, halogen, $C_1$-$C_4$alkyl or $C_1$-$C_4$haloalkyl and each of $R^7$, $R^8$ and $R^9$, independently of the others, is hydrogen, fluorine, bromine or chlorine and X is as defined in formula XI; (b) $R^5$ is hydrogen, methyl, $CF_3$, fluorine, chlorine or bromine, $R^6$ is hydrogen or $C_1$-$C_2$haloalkyl, each of $R^7$, $R^8$ and $R^9$, independently of the others, is hydrogen, fluorine or chlorine and X is sulfur, NH or oxygen; (c) $R^5$ is hydrogen, fluorine, chlorine or methyl, $R^6$ is $CF_3$, $R^7$ is hydrogen or chlorine, $R^8$ and $R^9$ are hydrogen and X is NH; or (d) $R^5$ is fluorine or chlorine, $R^6$ is $CF_3$, $R^7$ is chlorine, $R^8$ and $R^9$ are hydrogen and X is oxygen.

The compounds of formula XI are prepared by reacting a compound of formula IX with a compound of formula X at a temperature of 50° to 230° C., preferably 130° to 190° C. If one of the compounds is in liquid form, the reaction can be carried out without a solvent, otherwise inert solvents, for example N,N-dimethylformamide, bis(2-methoxyethyl) ether, tetraoxadodecane or 2-ethoxyethanol, are used.

The hydrogenation of compounds of formula XI is carried out at normal pressure of $H_2$ and in the presence of inert solvents, such as ethers (including tetrahydrofuran), esters and alcohols (also aqueous). The reaction takes place at a temperature of 0° to 80° C., preferably at 10° to 50° C.

The compounds of formula XI wherein n is 1 or 2 are obtained by oxidising the compounds of formula XI wherein n is 0 by methods known per se, for example with per-acids (for example m-chloroperbenzoic acid).

The intermediates of formulae II, III, IV and VI form part of the present invention. Owing to their structural characteristics they are ideally suited to the preparation of insecticidally and acaricidally active compounds.

The compounds of formula I are outstandingly suitable for controlling pests in and on animals and plants and generally have a systemic action, preferably when administered orally or by injection to domestic animals and productive livestock. They are especially effective against zooparasitic ectoparasites. The latter include insects of the orders Homoptera, Heteroptera, Diptera, Thysanoptera, Orthoptera, Anoplura, Siphonaptera, Mallophaga, Thysanura, Isoptera, Psocoptera and Hymenoptera and arachnida of the order Acarina, especially the Ixodidae family (ticks). Depending on the species, the ticks, during their development from the larva via the nymph to the imago, attack one host (monoxenous) or they fall off after reaching the nymph stage, find a new host and continue their development (dioxenous), or they parasitise a different animal during each stage (trioxenous).

The good pesticidal activity of the compounds of formula I according to the invention corresponds to a mortality of at least 50 to 60% of the mentioned pests. The insecticidal and acaricidal activity of the compounds of formula I resides less in the killing of the adult parasitic forms on the body of the host animal than in a development-inhibiting action on the larvae and eggs, so that the life cycle of the parasites is effectively interrupted.

Apart from their very favourable action against flies, for example *Musca domestica*, and mosquito larvae, compounds of formula I are especially suitable for controlling plant-destructive feeding insects in crops of ornamental and useful plants, especially in cotton crops (for example *Spodoptera littoralis* and *Heliothis virescens*) and in vegetable crops (for example *Leptinotarsa decemlineata*, *Pieris brassicae* and *Plutella xylostella*). Here too, attention is drawn especially to the larvicidal and ovicidal action of compounds of formula I. If compounds of formula I are ingested by adult insects with their food, then a reduced oviposition and/or a reduced hatching rate are (is) often observed, especially in the case of Coleoptera, for example *Anthonomus grandis*.

The compounds of formula I also exhibit a good anthelmintic activity. They are suitable for controlling parasitic nematodes, for example of the orders Rhabditida, Ascaridida, Spirurida and Trichocephalida, or for controlling cestodes of the orders Cyclophyllidae and Pseudophyllidae, or for controlling trematodes of the order Digenea in domestic animals and productive livestock, such as cattle, sheep, goats, horses, pigs, cats, dogs and poultry. They may be administered to the animals either as a single dose or in repeated doses, the individual doses being preferably 1 to 500 mg per kg body weight depending on the species of animal. Administration over a prolonged period will in many cases result in better action, or lower total doses will suffice.

The anthelmintic activity of the compounds of formula I resides less in the killing of the adult parasitic forms in the body of the host animal than in a development-inhibiting action on the larvae and on the eggs excreted with the faeces, so that the life cycle of the parasites is effectively interrupted.

The compounds of formula I are also effective against phytonematodes of the genera Meloidogyne, Heterodera, Pratylenchus, Ditylenchus, Radopholus, Rhizoglyphus and others.

The compounds of formula I are used in unmodified form or, preferably, together with the adjuvants conventionally employed in the art of formulation, and are therefore formulated in known manner e.g. into emulsifiable concentrates, dilutable or directly sprayable solutions, dilute emulsions, wettable powders, soluble powders, dusts, granulates, and also encapsulations in e.g. polymer substances. As with the nature of the compositions, the methods of application, such as spraying, atomising, dusting, scattering or pouring and especially oral administration and injection, are chosen in accordance with the intended objectives and the prevailing circumstances.

The compounds of formula I are administered to warm-blooded animals at rates of application of 0.01 to 100 mg/kg body weight. In the case of enclosed areas of cultivation they are applied in amounts of 10 g to 1000 g per hectare. They can also be used in pens, paddocks, stables and other localities.

The formulations, i.e. the compositions, preparations or mixtures containing the compound (active ingredient) of formula I are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the active ingredient to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$-alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 moles of ethylene oxide, or phospholipids.

The surfactants customarily employed in the art of formulation are described, inter alia, in the following publications:

"1986 International McCutcheon's Emulsifiers and Detergents", The Manufacturing Confectioner Publishing Co., Glen Rock, N.J., U.S.A. and Stache, H., Tensid-Taschenbuch, Hanser-Verlag, Munich, Vienna, 1981.

The pesticidal compositions usually contain 0.01 to 95%, preferably 0.1 to 80%, of a compound of formula I, 5 to 99.99% of a solid or liquid adjuvant, and 0 to 25%, preferably 0.1 to 25%, of a surfactant.

Whereas commercial products will preferably be formulated as concentrates, the end user will normally employ dilute formulations containing 1 to 10,000 ppm of active ingredient.

The present invention therefore also relates to pesticidal compositions that contain as active ingredient at least one compound of formula I together with customary carriers and/or dispersing agents.

The compositions may also contain further auxiliaries such as stabilisers, antifoams, viscosity regulators, binders, tackifiers as well as fertilisers or other active ingredients for obtaining special effects.

PREPARATION EXAMPLES

P-1:
N-[3-(3-chloro-5-trifluoromethylpyridyl-2-oxy)-4-chlorophenyl]-N'-[2,6-dichloro-3-aminobenzoyl]-urea (a) 2,6-dichloro-3-nitrobenzoic acid amide A solution of 12 g of fuming $HNO_3$ (d=1.52) in 11 ml of concentrated $H_2SO_4$ is added at room temperature over a period of 30 minutes to a solution of 30.4 g of 2,6-dichlorobenzoic acid amide in 60 ml of concentrated $H_2SO_4$ (d=1.83). After stirring for 2 hours at room temperature, the reaction mixture is added to ice/$H_2O$ and adjusted to a pH of ~6 with 30% NaOH and the precipitating crystals are isolated by filtration, affording 28.7 g of 2,6-dichloro-3-nitrobenzoic acid amide (m.p. 163°–165° C.).

(b) 2,6-dichloro-3-nitrobenzoyl isocyanate 3.5 ml of oxalyl chloride are added dropwise at room temperature over a period of 30 minutes to a suspension of 7.68 g of 2,6-dichloro-3-nitrobenzoic acid amide in 570 ml of methylene chloride. The batch is then heated at reflux temperature for 18 hours and the solvent is subsequently distilled off in vacuo, affording 8.6 g of crude 2,6-dichloro-3-nitrobenzoyl isocyanate which can be used directly in the subsequent reactions.

(c)
N-[3-(3-chloro-5-trifluoromethylpyridyl-2-oxy)-4-chlorophenyl]-N'-[2,6-dichloro-3-nitrobenzoyl]-urea 23.3 g of 3-(3-chloro-5-trifluoromethylpyridyl-2-oxy)-4-chloroaniline dissolved in 50 ml of methylene chloride are added at room temperature to 20.8 g of 2,6-dichloro-3-nitrobenzoyl isocyanate dissolved in 320 ml of methylene chloride and the batch is stirred for 19 hours. 200 ml of toluene are then added to the reaction mixture and approximately 80% of the solvent is removed in a rotary evaporator. The resulting precipitate is isolated by filtration, washed with a small amount of cold toluene and hexane and dried in vacuo, affording N-[3-(3-chloro-5-trifluoromethylpyridyl-2-oxy)-4-chlorophenyl]-N'-[2,6-dichloro-3-nitrobenzoyl]-urea in the form of a white crystaline power (m.p. 201°–203° C.).

(d)
N-[3-(3-chloro-5-trifluoromethylpyridyl-2-oxy)-4-chlorophenyl]-N'-[2,6-dichloro-3-aminobenzoyl]-urea 3.0 g of N-[3-(3-chloro-5-trifluoromethylpyridyl-2-oxy)-4-chlorophenyl]-N'-[2,6-dichloro-3-nitrobenzoyl]-urea are dissolved in 60 ml of tetrahydrofuran and hydrogenated for 6 hours at room temperature in the presence of 1 g of 5% rhodium/carbon. The reaction mixture is then filtered and the solvent is distilled off. The resulting crude product is recrystallised from diethyl ether/hexane, affording 2 g of N-[3-(3-chloro-5-trifluoromethylpyridyl-2-oxy)-4-chlorophenyl]-N'-[2,6-dichloro-3-aminobenzoyl]-urea in the form of colourless crystals (m.p. 207°–209° C.).

P-2:
N-[3-(3-chloro-5-trifluoromethylpyridyl-2-oxy)-4-chlorophenyl]-N'-[2,6-difluoro-3-(N-acetylamino)-benzoyl]-urea (a) 2,6-difluoro-3-nitrobenzoic acid amide Analogously to procedure (P-1a), 22.6 g of 2,6-difluoro-3-nitrobenzoic acid amide (m.p. 134°–135° C.) are obtained from 23.1 g of 2,6-difluorobenzoic acid amide.

(b) 2,6-difluoro-3-nitrobenzoyl isocyanate 2,6-difluoro-3-nitrobenzoyl isocyanate is prepared analogously to procedure (P-1b) from 2,6-difluoro-3-nitrobenzoic acid amide.

(c)

N-[3-(3-chloro-5-trifluoromethylpyridyl-2-oxy)-4-chlorophenyl]-N'-[2,6-difluoro-3-nitrobenzoyl]-urea A solution of 12.9 g of 3-(3-chloro-5-trifluoromethylpyridyl-2-oxy)-4-chloroaniline in 30 ml of ethylene chloride is added to a solution of 10.0 g of 2,6-difluoro-3-nitrobenzoyl isocyanate in 190 ml of ethylene chloride and the reaction mixture obtained is stirred for 5 hours at room temperature. The solvent is then removed, the residue is stirred with 70 ml of toluene and the resulting precipitate is isolated by filtration, affording 15.1 g of N-[3-(3-chloro-5-trifluoromethylpyridyl-2-oxy)-4-chlorophenyl]-N'-[2,6-difluoro-3-nitrobenzoyl]-urea in the form of colourless crystals (m.p. 186°–187° C.).

(d)

N-[3-(3-chloro-5-trifluoromethylpyridyl-2-oxy)-4-chlorophenyl]-N'-[2,6-difluoro-3-aminobenzoyl]-urea Analogously to procedure (P-1d), 10.6 g of N-[3-(3-chloro-5-trifluoromethylpyridyl-2-oxy)-4-chlorophenyl]-N'-[2,6-difluoro-3-aminobenzoyl]-urea (m.p. 181°–182° C.) are obtained from 15 g of N-[3-(3-chloro-5-trifluoromethylpyridyl-2-oxy)-4-chlorophenyl]-N'-[2,6-difluoro-3-nitrobenzoyl]-urea.

(e)

N-[3-(3-chloro-5-trifluoromethylpyridyl-2-oxy)-4-chlorophenyl]-N'-[2,6-difluoro-3-(N-acetylamino)-benzoyl]-urea 0.33 ml of acetyl chloride is added to a solution of 2.0 g of N-[3-(3-chloro-5-trifluoromethylpyridyl-2-oxy)-4-chlorophenyl]-N'-[2,6-difluoro-3-aminobenzoyl]-urea and 0.31 ml of pyridine in 38 ml of methylene chloride and the batch is stirred for 3 hours at 0° C. The resulting precipitate is isolated by filtration, washed with 1N HCl, water and methylene chloride and dried in vacuo, affording 1.1 g of N-[3-(3-chloro-5-trifluoromethylpyridyl-2-oxy)-4-chlorophenyl]-N'-[2,6-difluoro-3-(N-acetylamino)-benzoyl]-urea (m.p. 209°–211° C.).

P-3:

N-[3-(3-chloro-5-trifluoromethylpyridyl-2-oxy)-4-fluorophenyl]-N'-[2,6-difluoro-3-aminobenzoyl]-urea (a)

N-[3-(3-chloro-5-trifluoromethylpyridyl-2-oxy)-4-fluorophenyl]-N'-[2,6-difluoro-3-nitrobenzoyl]-urea 9.7 g of 3-(3-chloro-5-trifluoromethylpyridyl-2-oxy)-4-fluoroaniline dissolved in 10 ml of methylene chloride are added at room temperature to 8.6 g of 2,6-difluoro-3-nitrobenzoyl isocyanate (see P-2b) for preparation) dissolved in 300 ml of methylene chloride and the batch is stirred for 3 hours at room temperature. 300 ml of toluene are then added to the reaction mixture and approximately 80% of the solvent is distilled off in vacuo. The resulting precipitate is isolated by filtration and washed with a small amount of toluene and hexane, affording 11.9 g of N-[3-(3-chloro-5-trifluoromethylpyridyl-2-oxy)-4-fluorophenyl]-N'-[2,6-difluoro-3-nitrobenzoyl]-urea in the form of colourless crystals (m.p. 183°–185° C.).

(b)

N-[3-(3-chloro-5-trifluoromethylpyridyl-2-oxy)-4-fluorophenyl]-N'-[2,6-difluoro-3-aminobenzoyl]-urea 8.8 g of N-[3-(3-chloro-5-trifluoromethylpyridyl-2-oxy)-4-fluorophenyl]-N'-[2,6-difluoro-3-nitrobenzoyl]-urea are dissolved in 180 ml of tetrahydrofuran and hydrogenated for 17 hours at room temperature in the presence of 15 g of Raney nickel. The reaction mixture is then filtered and the solvent is distilled off in vacuo. The resulting crude product is recrystallised from diethyl ether, affording 6.7 g of N-[3-(3-chloro-5-trifluoromethylpyridyl-2-oxy)-4-fluorophenyl]-N'-[2,6-difluoro-3-aminobenzoyl]-urea in the form of colourless crystals (m.p. 174°–175° C.).

P-4:

N-[3-(3-chloro-5-trifluoromethylpyridyl-2-oxy)-4-chlorophenyl]-N'-[2,6-difluoro-3-(N-carboxy-propionylamino)-benzoyl]-urea A solution of 2.0 g of N-[3-(3-chloro-5-trifluoromethylpyridyl-2-oxy)-4-chlorophenyl]-N'-[2,6-difluoro-3-aminobenzoyl]-urea (see P-2d) for preparation), 0.46 g of succinic acid anhydride and 14 ml of tetrahydrofuran is stirred for 2 days at room temperature. The solvent is then distilled off in vacuo and the residue is stirred with 50 ml of methylene chloride. The resulting precipitate is isolated by filtration and washed with diethyl ether, affording N-[3-(3-chloro-5-trifluoromethylpyridyl-2-oxy)-4-chlorophenyl]-N'-[2,6-difluoro-3-(N-carboxy-propionylamino)-benzoyl]-urea in the form of a white powder (m.p. 223°–225° C.).

P-5:

N-[3-(3-chloro-5-trifluoromethylpyridyl-2-oxy)-4-chlorophenyl]-N'-[2,6-difluoro-3-(N-methylcarbamoylamino)-benzoyl]-urea A solution of 3.84 g of N-[3-(3-chloro-5-trifluoromethylpyridyl-2-oxy)-4-chlorophenyl]-N'-[2,6-difluoro-3-aminobenzoyl]-urea (see P-2d) for preparation), 0.27 ml of methyl isocyanate and 0.31 ml of pyridine in 50 ml of methylene chloride is stirred for 5 days at room temperature. The resulting precipitate is isolated by filtration, washed with a small amount of methylene chloride and diethyl ether and dried in vacuo, affording 1.47 g of N-[3-(3-chloro-5-trifluoromethylpyridyl-2-oxy)-4-chlorophenyl]-N'-[2,6-difluoro-3-(N-methylcarbamoylamino)-benzoyl]-urea (m.p. 209°–211° C.).

P-6:

N-(5-trifluoromethyl-2-pyridyl)-2-methyl-5-amino-aniline (a)

N-(5-trifluoromethyl-2-pyridyl)-2-methyl-5-nitroaniline 3.04 g (0.02 mmol) of 2-amino-4-nitrotoluene and 7.26 g (0.04 mol) of 2-chloro-5-trifluoromethylpyridine are stirred in the molten state for 5 hours at 160° C. After cooling, 200 ml of water are added thereto and the product is taken up in methylene chloride. The solvent is evaporated off and the residue is purified by column chromatography (silica gel, methylene chloride:hexane=2:1), affording 4.4 g of N-(5-trifluoromethyl-2-pyridyl)-2-methyl-5-nitroaniline (m.p. 103°–105° C.).

(b)

N-(5-trifluoromethyl-2-pyridyl)-2-methyl-5-aminoaniline 4.2 g of the compound obtained in (a) are hydrogenated at normal pressure and at 30°–35° C. with 4 g of Raney nickel in 80 ml of tetrahydrofuran. The catalyst is filtered off and the solvent is concentrated by evaporation. The residue is suspended in hexane and the resulting crystals are filtered and dried, affording 3.4 g of N-(5-trifluoromethyl-2-pyridyl)-2-methyl-5-aminoaniline in the form of a white powder (m.p. 113°–115° C.).

N-(5-trifluoromethyl-2-pyridyl)-2-methyl-5-aminoaniline can be used in Examples P-1 and P-2, instead of the pyridyloxyanilines used in (c), for the preparation of compounds in which X is NH.

P-7:
N-(3-chloro-5-trifluoromethyl-2-pyridyl)-2-chloro-5-aminoaniline (a)
N-(3-chloro-5-trifluoromethyl-2-pyridyl)-2-chloro-5-nitroaniline 3.4 g (0.02 mol) of 2-chloro-5-nitroaniline, 8.6 g (0.04 mol) of 2,3-dichloro-5-trifluoromethylpyridine and 400 mg of copper powder are maintained at 230° C. overnight in a small bomb tube (25 ml). After cooling, the crude product is purified by column chromatography (silica gel, petroleum ether:methylene chloride=6:1), affording 1.6 g of N-(3-chloro-5-trifluoromethyl-2-pyridyl)-2-chloro-5-nitroaniline in the form of a yellow powder (m.p. 122°–124° C.).

(b)
N-(3-chloro-5-trifluoromethyl-2-pyridyl-2-chloro-5-aminoaniline 1.4 g of the compound obtained in (a) are hydrogenated at normal pressure and at 30°–35° C. with 2 g of rhodium (5% on carbon) in 80 ml of tetrahydrofuran. The catalyst is filtered off and the solvent is concentrated by evaporation. The residue is suspended in petroleum ether and the resulting crystals are filtered and dried, affording 1.1 g of N-(3-chloro-5-trifluoromethyl-2-pyridyl)-2-chloro-5-aminoaniline in the form of a white powder (m.p. 111°–113° C.).

N-(3-chloro-5-trifluoromethyl-2-pyridyl)-2-chloro-5-aminoaniline can be used in Examples P-1 and P-2, instead of the pyridyloxyanilines used in (c), for the preparation of compounds in which X is NH.

The following compounds, which are listed in the Tables together with the compounds of the above Preparation Examples, are prepared analogously to the processes described above:

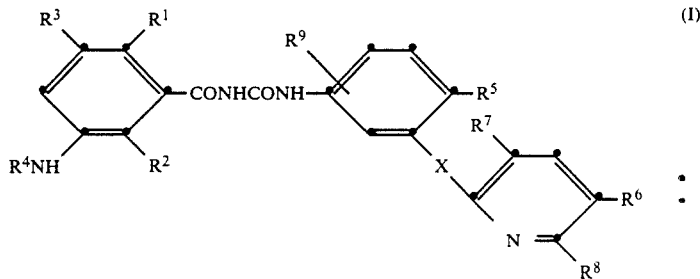
(I)

TABLE 1

| No. | $R^1$ | $R^2$ | $R^3$ | $R^4$ | $R^5$ | $R^6$ | $R^7$ | $R^8$ | $R^9$ | X | m.p. (°C.) |
|---|---|---|---|---|---|---|---|---|---|---|---|
| 1.1 | F | F | H | H | Cl | $CF_3$ | Cl | H | H | O | 181–182 |
| 1.2 | Cl | Cl | H | H | Cl | $CF_3$ | Cl | H | H | O | 207–209 |
| 1.3 | F | F | H | $COCH_3$ | Cl | $CF_3$ | Cl | H | H | O | 209–211 |
| 1.4 | F | F | H | $CONHCH_3$ | Cl | $CF_3$ | Cl | H | H | O | 209–211 |
| 1.5 | F | F | H | $CO(CH_2)_2COOH$ | Cl | $CF_3$ | Cl | H | H | O | 223–225 |
| 1.6 | F | F | H | H | F | $CF_3$ | Cl | H | H | O | 174–175 |
| 1.7 | F | F | H | H | Cl | $CF_3$ | Cl | Cl | H | O | 208–210 |
| 1.8 | F | F | H | H | Cl | $CF_3$ | H | H | F | O | 189–191 |
| 1.9 | F | F | H | H | Cl | $CF_2CCl_2F$ | Cl | H | H | O | 187–191 |
| 1.10 | F | F | H | H | $CH_3$ | $CF_3$ | Cl | H | H | NH | 202–204 |
| 1.11 | F | F | H | H | Cl | $CF_3$ | Cl | H | H | NH | 214–216 |
| 1.12 | F | F | H | H | H | $CF_3$ | Cl | H | H | S | 193–194 |
| 1.13 | F | F | H | H | H | $CF_3$ | H | H | H | S |  |

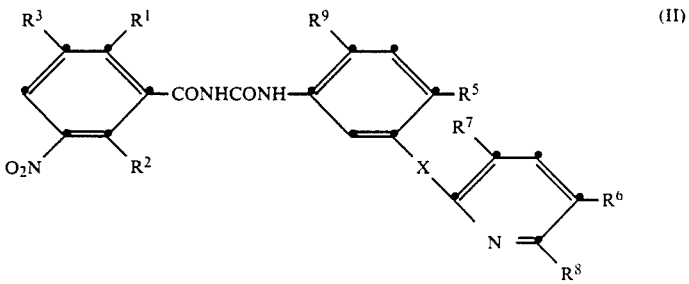
(II)

TABLE 2

| No. | $R^1$ | $R^2$ | $R^3$ | $R^5$ | $R^6$ | $R^7$ | $R^8$ | $R^9$ | X | m.p. (°C.) |
|---|---|---|---|---|---|---|---|---|---|---|
| 2.1 | F | F | H | Cl | $CF_3$ | Cl | H | H | O | 186–187 |

TABLE 2-continued

| No. | R¹ | R² | R³ | R⁵ | R⁶ | R⁷ | R⁸ | R⁹ | X | m.p. (°C.) |
|---|---|---|---|---|---|---|---|---|---|---|
| 2.2 | Cl | Cl | H | Cl | CF₃ | Cl | H | H | O | 201–203 |
| 2.3 | F | F | H | F | CF₃ | Cl | H | H | O | 183–185 |
| 2.4 | F | F | H | Cl | CF₃ | Cl | Cl | H | O | 188 (decomposition) |
| 2.5 | F | F | H | Cl | CF₃ | H | H | F | O | 195–201 |
| 2.6 | F | F | H | Cl | CF₂CCl₂F | Cl | H | H | O | 201–205 |
| 2.7 | F | F | H | CH₃ | CF₃ | Cl | H | H | NH | 212–214 |
| 2.8 | F | F | H | Cl | CF₃ | Cl | H | H | NH | 229–231 |
| 2.9 | F | F | H | H | CF₃ | Cl | H | H | S | 205–207 |
| 2.10 | F | F | H | H | CF₃ | H | H | H | S | |

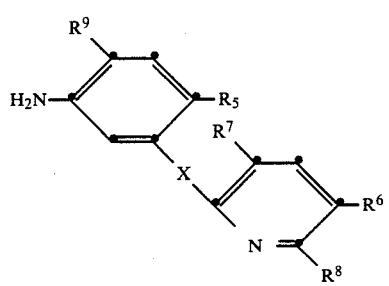

(III)

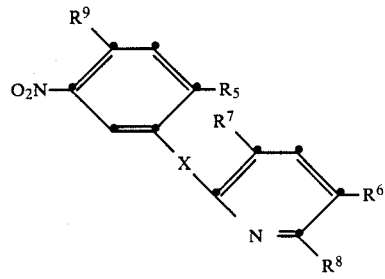

(XI)

TABLE 3

| No. | R⁵ | R⁶ | R⁷ | R⁸ | R⁹ | X | m.p. (°C.) |
|---|---|---|---|---|---|---|---|
| 3.1 | H | CF₃ | H | H | H | S | |
| 3.2 | H | CF₃ | Cl | H | H | S | 115–117 |
| 3.3 | H | CF₃ | H | H | H | NH | 106–109 |
| 3.4 | H | CF₃ | Cl | H | H | NH | 102–104 |
| 3.5 | F | CF₃ | H | H | H | NH | 105–107 |
| 3.6 | F | CF₃ | Cl | H | H | NH | 105–107 |
| 3.7 | Cl | CF₃ | H | H | H | NH | 117–119 |
| 3.8 | Cl | CF₃ | Cl | H | H | NH | 111–113 |
| 3.9 | CH₃ | CF₃ | H | H | H | NH | 113–115 |
| 3.10 | CH₃ | CF₃ | Cl | H | H | NH | 160–162 |

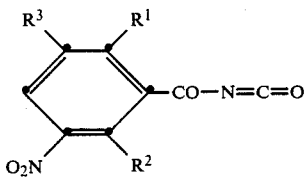

(IV)

TABLE 4

| No. | R¹ | R² | R³ |
|---|---|---|---|
| 4.1 | Cl | Cl | H |
| 4.2 | F | F | H |

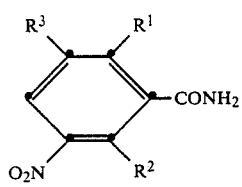

(VI)

TABLE 5

| No. | R¹ | R² | R³ | m.p. (°C.) |
|---|---|---|---|---|
| 5.1 | F | F | H | 134–135 |
| 5.2 | Cl | Cl | H | 163–165 |

| Formulation Examples for solid active ingredients of formula I (throughout, percentages are by weight) | | | |
|---|---|---|---|
| (F-1) Wettable powders | (a) | (b) | (c) |
| a compound of Table 1 | 25% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording a wettable powder which can be diluted with water to give suspensions of the desired concentration.

The powder can be administered with the feed.

| (F-2) Emulsifiable concentrate | |
|---|---|
| a compound of Table 1 | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| (F-3) Dusts | (a) | (b) |
|---|---|---|
| a compound of Table 1 | 5% | 8% |
| talcum | 95% | — |
| kaolin | — | 92% |

Ready-for-use dusts are obtained by mixing the active ingredient with the carrier and grinding the mixture in a suitable mill. Dusts can be applied directly or mixed with the feed.

| (F-4) Extruder granulate | |
|---|---|
| a compound of Table 1 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and granulated and then dried in a stream of air. Such granulates are also suitable as feed additives.

| (F-5) Coated granulate | |
|---|---|
| a compound of Table 1 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner. Such granulates are also suitable as feed additives.

| (F-6) Suspension concentrate | |
|---|---|
| a compound of Table 1 | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a | 75% |
| aqueous emulsion | 0.8% |
| water | 32% |

The finely ground active ingredient is intimately mixed with the adjuvants, giving a suspension concentrate from which suspensions of any desired concentration can be obtained by dilution with water. Suspension concentrates can also be administered orally to the animal ("drench").

| (F-7) Compacts | | |
|---|---|---|
| I | compound of Table 1 | 33.0% |
| | methylcellulose | 0.8% |
| | silicic acid (highly dispersed) | 0.8% |
| | corn starch | 8.4% |
| II | lactose (crystalline) | 22.5% |
| | corn starch | 17.0% |
| | microcrystalline cellulose | 16.5% |
| | magnesium stearate | 1.0% |

The adjuvants of phase I are granulated with the active ingredient with the addition of 16.5 parts of water and then mixed with the adjuvants of phase II. The mixture is compressed to form tablets or boli and dried.

| (F-8) Injectable solutions | | | |
|---|---|---|---|
| (a) | I | compound of Table 1 | 5 g |
| | II | polyoxyethylated castor oil, hydrogenated (40 moles of ethylene oxide) | 30 g |
| | III | N-methylpyrrolidone | ad 100 ml |
| (b) | I | compound of Table 1 | 5 g |
| | II | polyoxyethylated castor oil, hydrogenated (40 moles of ethylene oxide) | 15 g |
| | III | N-methylpyrrolidone | ad 100 ml |
| (c) | I | compound of Table 1 | 5 g |
| | II | polyoxyethylated castor oil, hydrogenated (40 moles of ethylene oxide) | 20 g |
| | | benzyl alcohol | 10 g |
| | | DMSO (dimethyl sulfoxide) | 20 g |
| | III | N-methylpyrrolidone | ad 100 ml |

The active ingredient is mixed with a proportion of component III and is completely dissolved while stirring and optionally while heating slightly. After the addition of II and intimate mixing, the mixture is made up to the desired volume with III. The finished mixture is sterile-filtered (membrane filtration 0.22 μm) and sterilised for 15 minutes at 121° C.

In all of the Examples, a proportion of the compound of Table 1 can be replaced by other anthelmintics, insecticides or acaricides.

BIOLOGICAL EXAMPLES (B-1) Tests on sheep infected with *Haemonchus contortus*

(a) Action on larval development in the host

A specific amount of the test compound is administered daily for 10 days to sheep by means of a stomach tube. The dosages vary from 0.01 to 100 mg per kg live weight. The infection with infectious *H. contortus* larvae takes place on the 2nd day after the start of treatment.

The action is evaluated by counting the eggs in faeces samples which are taken from the sheep rectally from 21 to 35 days after infection. The action is demonstrated in that the faeces samples from the sheep treated with the compound of formula I contain no worm eggs in contrast to the samples taken from the control animals. The absence of worm eggs shows that H. contortus cannot develop normally.

(b) Action on *H. contortus* eggs

The compound of formula I is administered daily for 14 days by means of a stomach tube at a dosage of 10 mg per kg live weight to sheep severely infected with *H. contortus* adults.

The action is evaluated by counting the infectious larvae in incubated faeces samples which are taken from the sheep rectally from the 3rd to the 21st day after the start of treatment. The action is demonstrated in that no larvae are produced from eggs deposited from the 3rd to the 14th day of treatment whereas they are produced from eggs taken from untreated control animals and from eggs deposited after treatment is discontinued.

(B-2) Action against eggs of the liver fluke *Fasciola hepatica*

*F. hepatica* eggs in aqueous medium are exposed to concentrations of 7.5, 75 and 750 ppm of the compound of formula I and stored in the dark at room temperature for 15 days.

Examination of the eggs under a microscope after 15 days shows that, in the case of the two higher concentrations, no miracidia develop and the eggs are totally deformed.

In tests (B-1a) and (b) and (B-2), the compounds of formula I exhibit pronounced development-inhibiting action on the eggs, larvae and miracidia (inhibition 95 to 100% compared with the untreated host).

(B-3) Reproduction-inhibiting action on ticks

Fresh females of the tick species *Boophilus microplus* which are replete with blood are affixed in the dorsal position to PVC plates in rows of ten insects each and are covered with a cotton wool swab. 10 ml of the aqueous test solution is then poured over each row. One hour later the cotton wool swab is removed and the ticks are dried overnight at 24° C. After drying, the ticks are kept for 4 weeks at 28° C. and 80% humidity until oviposition has taken place and the larvae have started to hatch.

Each test compound is tested at 5 concentrations of from 1000 to 62 ppm (dilution factor 2). The acaricidal action manifests itself either in the female as mortality or sterility or in the eggs by inhibition of embryogenesis or hatching. All the compounds are tested against two different strains of tick, the normally sensitive strain YEERONGPILLY and the OP-resistant strain BIARRA.

The activity of a compound is evaluated on the basis of the lowest concentration still approximately fully active (IR 90~90% inhibition of reproduction).

In this test, compounds of formula I, for example compounds Nos. 1.1, 1.6, 1.7, 1.9 and 1.12, exhibit a more than 90% reproduction-inhibiting action at concentrations of 62 ppm.

(B-4) Influence on the reproduction of *Anthomonus grandis*

*Anthomonus grandis* adults that are no older than 24 hours after leaving the last pupal case are transferred in groups of 25 beetles to barred cages. The cages occupied by the beetles are then immersed for 5 to 10 seconds in a solution containing 800 ppm of the test compound in acetone. After the beetles have dried, they are placed in covered dishes containing feed and left for copulation and oviposition. Egg deposits are flushed out with running water twice to three times weekly, counted, disinfected by putting them for 2 to 3 hours into an aqueous disinfectant, and then placed in dishes containing a suitable larval feed. After 7 days a check is carried out to establish whether larvae have developed from the deposited eggs.

The duration of the reproduction-inhibiting effect of the test compounds is determined by monitoring the egg deposits of the beetles further, i.e. over a period of about 4 weeks. Evaluation is made by assessing the reduction in the number of deposited eggs and larvae hatched from them in comparison with untreated controls.

Compounds of formula I exhibit a good reproduction-inhibiting activity in this test.

(B-5) Action against *Aëdes aegypti*

A concentration of 12.5 ppm is obtained by pipetting a specific amount of a 0.1% solution of the test compound is acetone onto the surface of 150 ml of water in a culture vessel. After the acetone has evaporated, 30 to 40 2-day-old Aëdes larvae are put into the vessel. Mortality counts are made after 2 and 7 days.

Compounds of formula I exhibit good activity in this test.

(B-6) Action against blowflies

Freshly deposited eggs of the blowfly species *Lucilia sericata* and *L. cuprina* are placed in small portions (30 to 50 eggs) into each of a number of test tubes in which 4 ml of nutrient medium have been mixed with 1 ml of test solution at the intermediate dilution of the active ingredient necessary to obtain the final concentration. After inoculating the culture medium, the test tubes are sealed with cotton wool plugs and are then incubated in an incubator at 30° C. for 4 days. In the untreated medium, larvae about 1 cm in length (stage 3) have developed by the end of this 4-day period. When a compound is active the larvae are by the end of this period either dead or distinctly retarded. Four tests are carried out simultaneously with concentrations of 100, 40, 16 and 6.4 ppm, respectively. The activity is measured according to the lowest concentration that is still fully active (LC 100).

The good larvicidal action of compounds Nos. 1.1, 1.6, 1.8 and 1.9 of formula I is demonstrated in this test by 100% mortality of the larvae after, at the most, 96 h at concentrations of 6.4 ppm.

(B-7) Action against *Musca domestica*

50 g of freshly prepared CSMA nutrient substrate for maggots are charged into each of a number of beakers. 5 ml of a 1% by weight solution of the test compound in acetone are pipetted onto the nutrient substrate in the beaker. The substrate is then thoroughly mixed and the acetone subsequently allowed to evaporate over a period of at least 20 hours.

Then 25 one-day-old maggots of *Musca domestica* are put into each of the beakers containing the treated nutrient substrate. After the maggots have pupated, the pupae are separated from the substrate by flushing them out with water. The number of pupae flushed out reflects the toxic effect of the test compound on the maggot development.

The pupae are deposited in a container closed with a perforated top. A count is made after 10 days of the number of flies that have hatched out of the pupae.

The compounds of formula I exhibit good activity at concentrations of over 40 ppm in this test.

(B-8a) Insecticidal stomach toxicant action

Cotton plants in the cotyledon stage are sprayed with an aqueous emulsion (obtained from a 10% emulsifiable concentrate) containing 100 ppm of the test compound.

After the coating has dried, the cotton plants are populated with *Spodoptera littoralis* larvae in the $L_1$ stage. The test is carried out at 26° C. and 50% relative humidity. The mortality and disorders in the larvae's development and shedding are determined at intervals of 24 hours.

Compounds of formula I, for example compounds 1.1, 1.3, 1.4, 1.6, 1.7, 1.8 and 1.9, exhibit more than 80% activity at a concentration of 100 ppm.

(B-8b) Ovicidal action against *Spodoptera littoralis*

Eggs of *Spodoptera littoralis* deposited on filter paper are cut out of the paper and immersed in a 0.1% by weight solution of the test compound in an acetone/water mixture (1:1). The treated egg deposits are then removed from this mixture and placed in plastic dishes at 28° C. and 60% relative humidity.

After 5 days, the hatching rate, i.e. the number of larvae that have developed from the treated eggs, is determined.

Compounds of formula I exhibit good activity in this test.

(B-9) Action against fleas

Dogs having the proven ability to support a flea population permanently are infested with 100 cat fleas *Ctenocephalides felis* Bouche. The infested dogs are then divided into 3 groups of 2 animals. The dogs in two of the groups are treated orally on 10 consecutive days with 5 mg of test compound/kg body weight. The test compound is administered in the form of an aqueous suspension (by means of a syringe). The third group of animals is not treated and serves as a control group.

After 3, 8 and 10 days, the eggs of the fleas are collected from the paper which is under the dog cages. The eggs are counted, placed on a medium suitable for the culture of larvae and incubated. A count is made of the resulting pupae and fully grown fleas.

Compounds of Table 1, for example compounds 1.1, 1.6 and 1.12, exhibit more than 50% activity at a dose of 50 mg kg-1 day-1.

(B-10) Comparison with the Prior Art

The present invention is compared with the prior art on the basis of the two primary representatives (A) and (B) mentioned hereinafter.

Compound of the prior art:

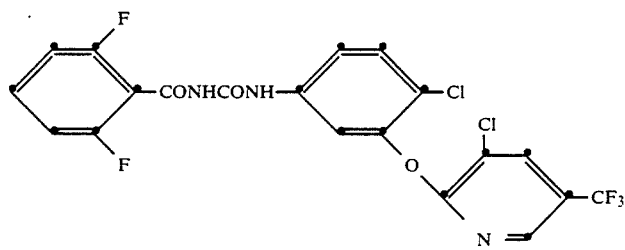

compound no. 17
from EP 0 079 311

Compound of the present invention:

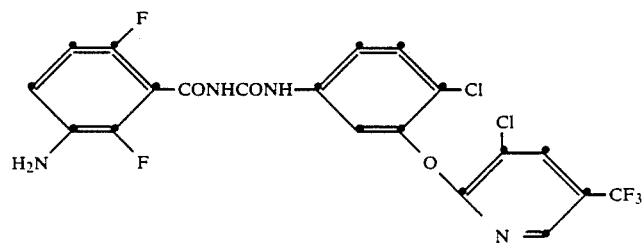

compound no. 1.1

(a) Physico-chemical charateristics of compounds (A) and (B)

| Solubilities: | (A) | (B) |
|---|---|---|
| water (ppm) | 0.02 | 0.11 |
| hexane (ppm) | 3 | ~60 |
| n-octanol (%) | 0.065 | 0.56 |
| isopropanol (%) | 0.09 | 0.30 |

(b) Bio-availability of compounds (A) and (B)

As a measure of bio-availability, the blood plasma level of the compounds is determined on several days after the injection of calves with, in each case, 1 mg of compound/kg body weight.

| | Blood plasma level [ppb active ingredient] | | | |
|---|---|---|---|---|
| | (A) | | (B) | |
| day | calf 1 | calf 2 | calf 3 | calf 4 |
| 1 | 7 | 5 | 126 | 185 |
| 7 | 3 | 4 | 48 | 66 |
| 14 | 4 | 9 | 16 | 27 |
| 21 | 7 | 10 | 10 | 12 |
| 28 | 6 | 5 | 5 | 6 |
| 35 | 6 | 10 | 2 | 4 |
| 42 | 9 | 6 | 0 | 0 |
| 49 | 4 | 4 | 0 | 0 |
| 56 | 5 | 5 | 0 | |
| 63 | 4 | 6 | | 0 |
| 70 | 7 | 5 | | 0 |
| 77 | 5 | 2 | | 0 |
| 84 | 7 | 7 | | 0 |

1. The concentration of compound (A) (prior art) in the blood reaches maximum values of from 7 to 10 ppb. Although this blood plasma level is maintained over a relatively long period, its absolute value is to be regarded as low.

2. When compound (B) (compound 1.1 of the present invention) is administered, a high concentration in the blood plasma is reached very rapidly. In addition, after only 35 to 42 days, measurable amounts of active ingredient are no longer detected.

Thus, very rapidly after administration, compound (B) produces higher blood plasma values and a distinctly better bio-availability than does compound (A). (B) is also excreted considerably more rapidly than (A) and therefore has a lesser adverse effect on the productive livestock treated.

What is claimed is:

1. A compound of formula I

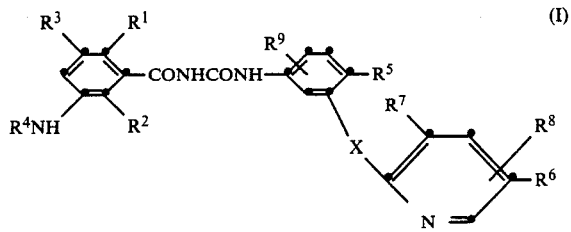

wherein
each of $R^1$, $R^2$, $R^3$, $R^7$, $R^8$ and $R^9$, independently of the others, is H or halogen,
$R^4$ is H, $R^{10}CO$— or $R^{11}NHCO$— wherein $R^{10}$ is a $C_1$–$C_4$ alkyl group which is unsubstituted or substituted by one to three identical or different substituents selected from the group consisting of halogen, $C_1$–$C_4$ alkoxy,
$C_1$–$C_4$ acyloxy and —COOG, wherein G is H, an alkali metal cation or an alkaline earth metal cation, and $R^{11}$ is an unsubstituted or halo-substituted $C_1$–$C_4$ alkyl or phenyl group,
each of $R^5$ and $R^6$, independently of the other, is H, halogen, $C_1$–$C_6$ or $C_1$–$C_6$ and
X is 0 or S(0)n wherein n is 0, 1 or 2.

2. A compound according to claim 1, wherein $R^4$ is hydrogen and each of $R^5$ and $R^6$, independently of the other, is hydrogen, halogen, $C_1$–$C_4$ alkyl or $C_1$–$C_4$ haloalkyl and $R^1$, $R^2$, $R^3$, $R^7$, $R^8$, $R^9$ and X are as defined in claim 1.

3. A compound according to claim 1, wherein $R^4$ is $R^{10}CO$— or $R^{11}NHCO$—.

4. A compound according to claim 1, wherein $R^4$ is hydrogen and X is oxygen.

5. A compound according to claim 1, wherein $R^4$ is hydrogen and X is S(0)n.

6. A compound according to claim 1, wherein each of $R^1$ and $R^2$, independently of the other, is fluorine or chlorine, $R^3$ is hydrogen, fluorine or chlorine, $R^4$ is hydrogen, $R^{10}CO$— or $R^{11}NHCO$— wherein $R^{10}$ is $C_1$–$C_4$ alkyl that is unsubstituted or substituted by —COOG, each of $R^5$ and $R^6$, independently of the other, is hydrogen, halogen, $C_1$–$C_2$ alkyl or $C_1$–$C_2$ haloalkyl and each of $R^7$, $R^8$ and $R^9$, independently of the others, is hydrogen, fluorine, bromine or chlorine.

7. A compound according to claim 6, wherein $R^1$ and $R^2$ are fluorine.

8. A compound according to claim 6, wherein $R^3$ and $R^4$ are hydrogen.

9. A compound according to claim 1, wherein $R^1$ and $R^2$ are fluorine.

10. A compound according to claim 1, wherein $R^1$ and $R^2$ are fluorine, $R^3$ and $R^4$ are hydrogen, $R^5$ is hydrogen, methyl, $CF_3$, fluorine, chlorine or bromine, $R^6$ is hydrogen or $C_1$–$C_2$ haloalkyl and each of $R^7$, $R^8$ and $R^9$, independently of the others, is hydrogen, fluorine or chlorine.

11. A compound according to claim 10, wherein X is oxygen.

12. A compound according to claim 10, wherein X is sulfur.

13. A compound according to claim 1, wherein $R^1$ and $R^2$ are fluorine, $R^3$ and $R^4$ are hydrogen, $R^5$ is fluorine or chlorine, $R^6$ is $CF_3$, $R^7$ is chlorine, $R^8$ and $R^9$ are hydrogen and X is oxygen.

14. A compound according to claim 1, wherein $R^1$ and $R^2$ are fluorine, $R^3$ and $R^4$ are hydrogen, $R^5$ is fluorine or chlorine, $R^6$ is $CF_3$, $R^7$ is chlorine, $R^8$ and $R^9$ are hydrogen and X is sulfur.

15. A compound according to claim 14, wherein $R^3$ is halogen, $R^7$ is fluorine and each of $R^8$ and $R^9$, independently of the other, is fluorine or chlorine.

16. N-[3-(3-chloro-5-trifluoromethylpyridyl-2-oxy)-4-fluorophenyl]-N'-[2,6-difluoro-3-aminobenzoyl]-urea, N-[3-(3-chloro-5-trifluoromethylpyridyl-2-oxy)-4-chlorophenyl]-N'-[2,6-dichloro-3-aminobenzoyl]-urea, N-[3-(3-chloro-5-trifluoromethylpyridyl-2-oxy)-4-chlorophenyl]-N'-[2,6-difluoro-3-aminobenzoyl]-urea, N-[3-(3-chloro-5-trifluoromethylpyridyl-2-oxy)-4-chlorophenyl]-N'-[2,6-difluoro-3-(N-methylcarbamoylamino)benzoyl]-urea, N-[3-(3-chloro-5-trifluoromethylpyridyl-2-oxy)-4-chlorophenyl]-N'-[2,6-difluoro-3-(N-acetylcarbamoylamino)benzoyl]-urea, N-[3-(3-chloro-5-trifluoromethylpyridyl-2-oxy)-4-chlorophenyl]-N'-[2,6-difluoro-3-(N-carboxypropionylamino)benzoyl]-urea, and N-[3-(3-chloro-5-trifluoromethylpyridyl-2-thio)-4-chlorophenyl]-N'-[2,6-difluoro-3-aminobenzoyl]-urea according to claim 1.

17. N-[3-(3-chloro-5-trifluoromethylpyridyl-2-oxy)-4-chlorophenyl]-N'-[2,6-difluoro-3-aminobenzoyl]-urea according to claim 1.

18. N-[3-(3-chloro-5-trifluoromethylpyridyl-2-oxy)-4-fluorophenyl]-N'-[2,6-difluoro-3-aminobenzoyl]-urea according to claim 1.

19. N-[3-(3-chloro-5-trifluoromethylpyridyl-2-thio)-4-chlorophenyl]-N'-[2,6-difluoro-3-aminobenzoyl]-urea according to claim 1.

20. A method of controlling parasites or insect pests that attack livestock or domestic animals, which comprises applying externally a parasiticidally or insecticidally effective amount of a compound of formula I according to claim 1 to the livestock.

21. A method of controlling parasites or insect pests that attack livestock or domestic animals, which comprises administering internally a paraciticically or insecticidally effective amount of a compound of formula I according to claim 1 to the livestock.

22. A composition for controlling ectoparasites, endoparasites or insect pests which comprises an effective amount of a compound of formula I according to claim 1 and a carrier.

* * * * *